United States Patent [19]

Lürssen et al.

[11] 4,140,518

[45] Feb. 20, 1979

[54] AGENTS FOR REGULATING PLANT GROWTH

[75] Inventors: Klaus Lürssen, Berg.Gladbach; Ulrich Holtschmidt; Günter Schwarzmann, both of Essen, all of Fed. Rep. of Germany

[73] Assignee: Bayer Aktiengesellschaft, Leverkusen, Fed. Rep. of Germany

[21] Appl. No.: 872,989

[22] Filed: Jan. 27, 1978

[30] Foreign Application Priority Data

Feb. 17, 1977 [DE] Fed. Rep. of Germany ....... 2706838

[51] Int. Cl.² .......................... A01N 5/00; A01N 9/22
[52] U.S. Cl. .......................................... 71/92; 71/76; 71/78
[58] Field of Search ................................ 71/92, 76, 78

[56] References Cited

U.S. PATENT DOCUMENTS

2,710,870   6/1955   Lawson .................................... 71/92

FOREIGN PATENT DOCUMENTS

2442706   2/1976   Fed. Rep. of Germany.
42-9473   5/1967   Japan.

*Primary Examiner*—Catherine L. Mills
*Attorney, Agent, or Firm*—Sprung, Felfe, Horn, Lynch & Kramer

[57] ABSTRACT

Novel imidazole derivatives, the use of certain imidazole derivatives as plant growth regulants and the preparation of certain new imidazole derivatives.

11 Claims, No Drawings

AGENTS FOR REGULATING PLANT GROWTH

BACKGROUND OF THE INVENTION

The present invention relates to new imidazole derivatives, use of imidazole derivatives as plant growth regulants and preparation of new imidazole derivatives.

It has already been disclosed in German Offenlegungsschrift No. 2,442,706 that certain imidazole derivatives possess a microbicidal activity. In addition, it has been disclosed in U.S. Pat. No. 3,156,554 that certain 2-halogeno-ethyl-trialkylammonium halides have plant growth regulating properties. Thus, it is possible to influence plant growth, for example, with the aid of (2-chlorethyl)-trimethylammonium chloride. However, the activity of this substance is not always sufficient, especially when low application amounts are used.

SUMMARY OF THE INVENTION

It has now been found that the imidazole derivatives of the general formula

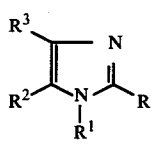
(I), in which
R represents hydrogen or alkyl with 1 to 4 carbon atoms,
$R^1$ represents alkyl,
$R^2$ represents hydrogen or methyl and
$R^3$ represents hydrogen or methyl,
have powerful plant growth-regulating properties.

Accordingly, the present invention provides a method of regulating the growth of plants, which comprises applying to the plants, or to a habitat thereof, a compound of the formula (I) alone or in admixture with a diluent or carrier.

The invention also provides plants, the growth of which has been regulated by their being grown in areas in which immediately prior to and/or during the time of the growing a compound of the formula (I) was applied alone or in admixture with a diluent or carrier.

Preferably, in formula (I), R represents hydrogen or unbranched alkyl with 1 to 3 carbon atoms and $R^1$ represents alkyl with 8 to 16 carbon atoms.

Surprisingly, the imidazole derivatives which can be used according to the invention exhibit a better plant growth-regulating activity than (2-chloroethyl)-trimethylammonium chloride, which is known from the state of the art and which is a substance having the same type of action, the activity of which is acknowledged as good. The substances which can be used according to the invention thus represent a valuable enrichment of the art.

Examples which may be mentioned of the active compounds which can be used according to the invention are: 1-dodecyl-2-methyl-imidazole, 1-octyl-2-ethyl-imidazole, 1-dodecyl-2-ethyl-imidazole, 1-octyl-2-propyl-imidazole, 1-dodecyl-2-propyl-imidazole, 1-hexadecyl-2-methyl-imidazole, 1-hexadecyl-2-ethyl-imidazole, 1-hexadecyl-2-propylimidazole, 1-hexadecyl-imidazole, 1-dodecyl-2,4-dimethylimidazole and 1-dodecyl-2,5-dimethyl-imidazole.

Some of the imidazole derivatives of the formula (I) which can be used according to the invention are known (see German Offenlegungsschrift No. 2,442,706). However, their use for regulating plant growth has not been described in the literature.

Certain of the imidazole derivatives which can be used according to the invention have not hitherto been described in the literature; however, they can be prepared in a simple manner by known methods. For example, they are obtained by reacting imidazoles of the general formula

in which
R, $R^2$ and $R^3$ have the meanings stated above, with alkyl halides of the general formula
$$I R^1- X \qquad (III),$$

in which
$R^1$ has the meaning stated above and X represents chlorine or bromine,
in the presence of a strong base, and optionally in the presence of a diluent, at temperatures between 100° C and 200° C., preferably between 120° C and 180° C.

Preferred strong bases are alkali metal hydroxides, for example sodium hydroxide and potassium hydroxide.

All the customary inert organic solvents with sufficiently high boiling points can be employed as the diluents. Dimethylformamide is preferably used.

In carrying out the process, 1 to 4 moles of an imidazole of the formula (II) and at least 1 mole of a strong base are generally employed per mole of an alkyl halide of the formula (III). In general, the compounds of the formula (I) are isolated by separating off the solid inorganic constituents after the reaction has ended, and subjecting the mixture which remains to fractional distillation.

Both the imidazoles of the formula (II) and the alkyl halides of the formula (III) are known or can be prepared by known methods.

The compounds according to the present invention engage in the metabolism of plants and can therefore be employed as growth regulators.

Experience to date of the mode of action of plant growth regulators has shown that an active compound can exert one or several different actions on plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended positively to influence the crop plants in the desired manner.

Plant growth-regulating compounds can be employed, for example, to inhibit vegetative plant growth. Such inhibition of growth is inter alia of economic interest in the case of grasses since, by repressing the growth of grass, it is possible, for example, to reduce the frequency of cutting the grass in ornamental gardens, parks and sports grounds or at verges. The inhibition of growth of herbaceous and woody plants at verges and in the vicinity of overland pipelines or, quite generally, in areas in which heavy growth is undesired, is also of importance.

The use of growth regulators to inhibit the growth in length of cereals is also important, since by shortening the stem the danger of lodging of the plants before harvesting is reduced or completely eliminated. Furthermore, growth regulators can strengthen the stem of cereals, which can counteract lodging.

In the case of many crop plants, inhibition of the vegetative growth permits denser planting of the crop, so that a greater yield per area of ground can be achieved.

A further mechanism of increasing the yield by means of growth inhibitors is based on the fact that the nutrients benefit blossoming and fruit formation to a greater extent, whilst vegetative growth is restricted.

Promotion of vegetative growth can also frequently be achieved with growth regulators. This is of great utility if it is the vegetative parts of the plants which are harvested. Promoting the vegetative growth can, however, also simultaneously lead to a promotion of generative growth, so that, for example, more fruit, or larger fruit, is formed.

Increases in yield can in some cases also be achieved by affecting the plant metabolism, without noticeable changes in vegetative growth. Growth regulators can furthermore produce a change in the composition of the plants so as to bring about better quality of the harvested products. Thus it is possible, for example, to increase the content of sugar in sugar beet, sugar cane, pineapples and citrus fruit or to increase the protein content in soya or cereals.

Parthenocarpous fruit can be formed under the influence of growth regulators. Furthermore, the gender of the flowers can be influenced.

Using growth regulators it is also possible favourably to influence the production or the efflux of secondary plant materials. The stimulation of latex flow in rubber trees may be mentioned as an example.

During the growth of the plant, lateral branching can also be increased, by using growth regulators, through chemical breaking of the apical dominance. There is interest in this, for example, in the case of plant propagation by cuttings. However, it is also possible to inhibit the growth of side shoots, for example to prevent the formation of side shoots in tobacco plants after decapitation and thus to promote leaf growth.

The amount of leaf on plants can be controlled, under the influence of growth regulators, so that defoliation of the plants at a desired point in time is achieved. Such defoliation is of interest to facilitate mechanical harvesting, for example of grapes or cotton, or to lower the transpiration at a point in time at which the plant is to be transplanted.

Premature shedding of fruit can be prevented by the use of growth regulators. However, it is also possible to promote the shedding of fruit— for example in the case of table fruit— in the sense of a chemical thinning out, up to a certain degree. Growth regulators can also be used to reduce the force required to detach the fruit from crop plants at harvest time so as to permit mechanical harvesting of the plants or facilitate manual harvesting.

Using growth regulators it is furthermore possible to achieve an acceleration or retardation of ripening of the harvest product, before or after harvesting. This is of particular advantage since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators it is also possible to influence the latent period of seeds or buds of plants, that is to say the endogenic annual rhythm, so that the plants, such as, for example, pineapple or decorative plants in nurseries, germinate, shoot or blossom at a time at which they normally show no readiness to do so.

Using growth regulators it is also possible to achieve a delay in the shooting of buds or the germination of seeds, for example to avoid damage by late frosts in regions where frost is a hazard.

Growth regulators can also produce halophilism in crop plants. This provides the preconditions for being able to cultivate plants on soils containing salt.

Using growth regulators, it is also possible to induce frost resistance and drought resistance in plants.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

The active compounds according to the instant invention can be utilized, if desired, in the form of the usual formulation or compositions with conventional inert (i.e., plant compatible) diluents or extenders, i.e., diluents, carriers or extenders of the type usable in conventional plant growth formulations or compositions, e.g. convention dispersible carrier vehicles such as gases, solutions, emulsions, wettable powders, suspensions, powder dusting agents, foams, pastes, soluble powders, granules, aerosols, suspension-emulsion concentrates, seedtreatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional dispersible liquid diluent carriers and/or dispersible solid carriers optionally with the use of carrier vehicle assistants, e.g., conventional surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons (dichlorodifluoromethane or trichlorofluoromethane) as well as butane, propane, nitrogen and carbon dioxide; inert dipsersible liquid diluent carriers, including inert organic solvents, such as aromatic hydrocarbons (e.g. benzene, toluene, xylene, alkyl naphthalenes, etc.) halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.), as well as ethers and esters thereof (e.g. glycol monomethyl ether, etc.) amines (e.g. ethanolamine, etc.), amides (e.g dimethyl formamide, etc.), sulfoxides (e.g. dimethyl sulfoxide, etc.) acetonitrile, ketones (e.g. acetone. methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl, cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt molybdenum and zinc.

Such active compounds may be employed alone or in the form of mixtures with one another and/or with such solid and/or liquid dispersible carrier vehicles and/or with other known compatible active agents, especially other plant protection agents, such as other insecticides, acaricides, fungicides, bactericides, rodenticides and fertilizers, if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between 0.0000001–100, preferably 0.01–10% by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of active compound which is effective for the purpose in question and which is generally between about 0.0001–95%, and preferably 0.01–95%, by weight of the mixture, preferably 0.1 to 95%, more preferably 0.5 to 90 weight percent.

The amount of active compound used can vary within a fairly wide range. It depends essentially on the nature of the desired effect. In general, the amounts used are from 0.01 to 50 kg, especially 0.05 to 10 kg of active compound per hectare.

It will be seen that the usual methods of providing a harvested crop may be improved by the present invention.

The plant growth regulating activity of the compounds of this invention is illustrated by the following biotest Examples.

In these Examples, the compounds according to the present invention are each identified by the number (given in brackets) of the corresponding preparative Example, which will be found later in this specification.

The known comparison compounds are identified as follows:

(A) = 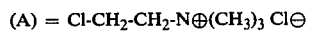

EXAMPLE A

Inhibition of growth/soya beans

Solvent: 10 parts by weight of methanol
Emulsifier: 2 parts by weight of polyoxyethylene sorbitan monolaurate To prepare a suitable preparation of active compound, 1 part by weight of active compound was mixed with the stated amounts of solvent and emulsifier and the mixture was made up to the desired concentration with water.

Young soya bean plants, at the stage in which the first secondary leaves had unfolded, were sprayed with the preparation of active compound until dripping wet. After 2 weeks, the additional growth was measured and the inhibition of growth in % of the additional growth of the control plants was calculated. 0% denoted growth corresponding to that of the control plants.

The active compounds, concentrations of the active compounds and results can be seen from the table which follows:

Table A

| Active compound | Active compound concentration in % | Inhibition of growth in % |
|---|---|---|
| — (control) | — | 0 |
| (A) | 0.05 | 0 |
| (1) | 0.05 | 45 |
| (2) | 0.05 | 60 |

EXAMPLE B

Inhibition of the growth of side shoots of tobacco

Solvent: 10 parts by weight of methanol
Emulsifier: 2 parts by weight of polyoxyethylene sorbitan monolaurate To prepare a suitable preparation of active compound, 1 part by weight of active compound was mixed with the stated amounts of solvent and emulsifier and the mixture was made up to the desired concentration with water.

The shoot tips of about 50 cm high tobacco plants were broken off. On the following day, the plants were sprayed with the preparations of active compound until dripping wet. After 3 weeks, the side shoots which had formed during this time were broken off. All the side shoots of one treatment were weighed. The weight of the side shoots of the treated plants was compared with the weight of the side shoots of the untreated control plant. 100% inhibition denoted the absence of side shoots and 0% denoted a growth of side shoots which corresponded to that of the control plants.

The active compounds, the concentrations of the active compounds and results can be seen from the table which follows:

Table B

| Inhibition of growth of side shoots of tobacco | | |
|---|---|---|
| Active compound | Active compound concentration in % | Inhibition of growth in % |
| — (control) | — | 0 |
| (4) | 0.2 | 65 |
| (3) | 0.2 | 43 |

EXAMPLE C

Influence on growth/cotton

Solvent: 10 parts by weight of methanol

Emulsifier: 2 parts by weight of polyoxyethylene sorbitan monolaurate

To prepare a suitable preparation of active compound, 1 part by weight of active compound was mixed with the stated amount of solvent and emulsifier and the mixture was made up to the desired concentration with water.

Young cotton plants in the 4-leaf stage were sprayed with the preparations of active compound until dripping wet. After 3 weeks, the additional growth was measured and the influence on growth in % of the additional growth of the control plants was calculated. 0% denoted growth corresponding to that of the control plants.

Positive values characterised promotion of growth compared to the control plants whilst negative values correspondingly indicated an inhibition of growth.

The active compounds, concentrations of the active compounds and results can be seen from the table which follows:

Table C

| Influence on growth/cotton | | |
|---|---|---|
| Active compound | Active compound concentration in % | Influence on growth in % |
| — (control) | — | 0 |
| (3) | 0.05 | −80* |

*The sprayed leaves dropped off

PREPARATIVE EXAMPLES

Example 1

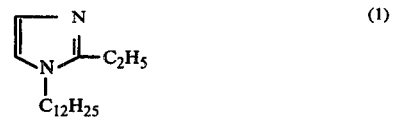

2 moles of 2-ethylimidazole and 2.2 moles of n-dodecyl bromide were heated to 130° C. for 30 minutes and 3.2 moles of NaOH were then added. The reaction mixture was then heated to 150° C. for a further 2 hours. The inorganic residue was filtered off and washed with benzene. The combined filtrates were distilled. During this, 468 g of 1-dodecyl-2-ethyl-imidazole passed over between 118° and 122° C. under a pressure of 0.5 mm Hg.

The compounds listed in the Table which follows were prepared in an analogous manner

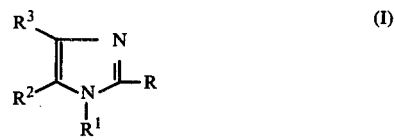

| Example | R | $R^1$ | $R^2$ | $R^3$ | Boiling point [° C/mm Hg] |
|---|---|---|---|---|---|
| 2 | $C_2H_5$ | $C_8H_{17}$ | H | H | 115–119/0.5 |
| 3 | $CH_3$ | $C_{12}H_{25}$ | H | H | 138–142/0.01 |
| 4 | H | $C_{16}H_{33}$ | H | H | 230/1.3 |
| 5 | $C_3H_7$ | $C_8H_{17}$ | H | H | 131–134/1.0 |
| 6 | $C_3H_7$ | $C_{12}H_{25}$ | H | H | 78–83/0.01 |

What we claim is:

1. A method of regulating the growth of plants which comprises applying to the plants, or to a habitat thereof, a plant growth regulatingly effective amount of an imidazole derivative of the general formula

in which
R represents hydrogen or alkyl with 1 to 4 carbon atoms,
$R^1$ represents alkyl, with 8 to 16 carbon atoms
$R^2$ represents hydrogen or methyl, and
$R^3$ represents hydrogen or methyl, alone or in admixture with a diluent or carrier.

2. A method according to claim 1, in which an imidazole derivative of the formula (I) is applied wherein R represents hydrogen or unbranched alkyl with 1 to 3 carbon atoms.

3. A method according to claim 1 wherein the imidazole derivative is applied to a plant selected from the group consisting of tobacco, soy bean and cotton.

4. A method according to claim 1 wherein said imidazole derivative is applied to an area of plant cultivation in an amount of 0.01 to 50 kg per hectare.

5. A method according to claim 4 wherein the imidazole derivative is applied in an amount of 0.05 to 10 kg per hectare.

6. A method according to claim 1 wherein said imidazole derivative has the formula

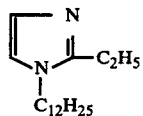
(1)

7. A method according to claim 1 wherein in said imidazole derivative R is ethyl, $R^1$ is $C_8H_{17}$ and $R^2$ and $R^3$ are each hydrogen.

8. A method according to claim 1 wherein in said imidazole derivative R is methyl, $R^1$ is $C_{12}H_{25}$ and $R^2$ and $R^3$ are each hydrogen.

9. A method according to claim 1 wherein in said imidazole derivative R is hydrogen, $R^1$ is $C_{16}H_{33}$ and $R^2$ and $R^3$ are each hydrogen.

10. A method according to claim 1 wherein in said imidazole derivative R is $C_3H_7$, $R^1$ $C_8H_{17}$, and $R^2$ and $R^3$ are each hydrogen.

11. A method according to claim 1 wherein in said imidazole derivative R is $C_3H_7$, $R^1$ is $C_{12}H_{25}$, and $R^2$ and $R^3$ are each hydrogen.

* * * * *

UNITED STATES PATENT AND TRADEMARK OFFICE
CERTIFICATE OF CORRECTION

PATENT NO. : 4,140,518
DATED : February 20, 1979
INVENTOR(S) : Lürssen et al.

It is certified that error appears in the above-identified patent and that said Letters Patent are hereby corrected as shown below:

Column 5, line 9, after "acetone" delete "." and insert -- , --.

Column 5, line 30, delete "," after "methyl".

Column 6, line 25, formula should read:

-- (A) = $Cl-CH_2-CH_2-\overset{\oplus}{N}(CH_3)_3$ $Cl^{\ominus}$ --.

Signed and Sealed this

*Tenth* Day of *July 1979*

[SEAL]

*Attest:*

*Attesting Officer*

LUTRELLE F. PARKER
*Acting Commissioner of Patents and Trademarks*